United States Patent [19]

Kauer

[11] Patent Number: 4,511,390
[45] Date of Patent: Apr. 16, 1985

[54] ARALKYLCARBAMOYL PEPTIDE ALCOHOLS

[75] Inventor: James C. Kauer, Kennett Square, Pa.

[73] Assignee: E. I. Du Pont de Nemours and Company, Wilmington, Del.

[21] Appl. No.: 503,295

[22] Filed: Jun. 10, 1983

[51] Int. Cl.³ .................... A01N 43/36; A01N 43/76; A01N 43/78; C07D 207/02
[52] U.S. Cl. ............................... 71/88; 71/90; 71/95; 548/201; 548/215; 548/536
[58] Field of Search ................ 548/536, 201, 215; 71/95, 90, 88

[56] References Cited

U.S. PATENT DOCUMENTS 4,217,130  8/1980  Tsuruta et al. .................. 548/536

FOREIGN PATENT DOCUMENTS 53-148530  12/1978  Japan .

OTHER PUBLICATIONS

Kyowa, C. A., 90:181578w, (1979).
Gruodiene et al., *Liet, TSR Aukst. Mokyklu Mokslo Darb. Biol.* 16:23–34, (1977).
Kida et al., *Agr. Biol. Chem.* 40:1551–1557, (1976).
Schloegl et al., *J. Med. Pharm. Chem.* 4:231–258, (1961).
Yoder et al., *Plant Physiol.* 52:513 to 517, (1973).
Yoder et al., *Plant Physiol.* 52:518–523, (1973).
Liesch et al., *Tetrahedron* 38:45 to 48, (1982).
Walton et al., *Biochem. Biophys. Res. Comm.* 107:785 to 794, (1982).
Kawai et al., *Biochem. Biophys. Res. Comm.* 111:398 to 403, (1983).

*Primary Examiner*—Joseph Paul Brust
*Attorney, Agent, or Firm*—Scott G. Hallquist

[57] ABSTRACT

Aralkylcarbamoyl peptide alcohols of the formula

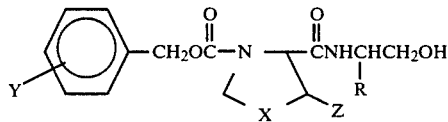

selectively stimulate nitrate and ammonium ion uptake by plants.

24 Claims, No Drawings

ARALKYLCARBAMOYL PEPTIDE ALCOHOLS

BACKGROUND OF THE INVENTION

The present invention concerns a novel class of aralkylcarbamoyl peptide alcohols which exhibit activity as enhancers of nutrient ion uptake by plant tissues.

Gruodiene et al., *Liet. TSR Aukst. Mokyklu Mokslo Darb. Biol.* 16:23–34 (1977) described experiments in which nitrate ion uptake of potted bean plants was enhanced by application of indoleacetic acid (IAA). Plant growth was stimulated, and levels of nitrate ion, ammonium ion, and amino nitrogen in root nodules were elevated in the plants treated with IAA.

Kida et al., *Agr. Biol. Chem.* 40:1551–1557 (1976) disclose use of certain N-acyl, N-alkyl, ester and amide derivatives of amino acids as inhibitors of root and shoot elongation in rice plants.

Schloegl et al., *J. Med. Pharm. Chem.* 4:231–258 (1961) disclose a snythesis of compounds of the formula

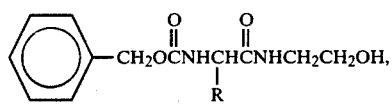

where R is phenyl or hydrogen. These compounds are intermediates in the synthesis of hydantoins.

SUMMARY OF THE INVENTION

The present invention provides compounds of the formula

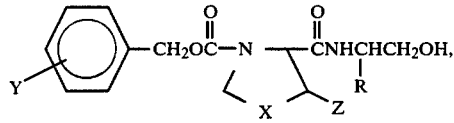

wherein
R is hydrogen or an alkyl group of 1 to 4 carbons;
X is $CH_2$, O or S;
Y is hydrogen or an ortho, meta or para substituent selected grom the group consisting of F, Cl, and alkyl groups of 1 to 4 carbons; and
Z is hydrogen or methyl.

In addition, the invention provides compositions comprising these compounds and methods of treating plants with the compositions to stimulate uptake of nitrate and ammonium ions.

DETAILED DESCRIPTION OF THE INVENTION

The carbobenzoxy peptide alcohols of the present invention are compounds of the formula

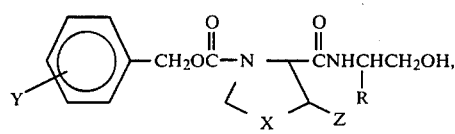

wherein R, X, Y and Z are as previously defined. Included within the scope of the present invention are racemic mixtures of the foregoing compounds, pure racemates, and optical antipodes thereof. "Alkyl," in the context of the present invention, includes both branched-chain and n-alkyl derivatives.

Of the compounds of the invention having a substituted phenyl moiety, those compounds in which Y is a para substituent are preferred on the basis of activity. However, the most active, and therefore most preferred compounds of the invention, are those in which X is $CH_2$, Y and Z are hydrogen, and R is an isopropyl or isobutyl group.

METHODS OF SYNTHESIS

The aralkylcarbamoyl peptide alcohols of the invention can be prepared by any of the amide-forming reactions known in the art for peptide synthesis. These reactions include:

(1) Mixed anhydride synthesis,
(2) Active ester synthesis, and
(3) Synthesis with condensing agents, e.g. carbodiimides, N-ethyl-5-phenylisoxazolium-3'-sulfonate (Woodward's Reagent K), or carbonyldiimidazole.

The following discussion illustrates application of each of the foregoing methods to the synthesis of N-carbobenzoxy-L-proly-L-leucinol, a compound of the invention.

1. Mixed Anhydride Synthesis

A mixed carbonic acid anhydride synthesis is a reliable and efficient method of preparing compounds of the invention, involving coupling of optically active amino acids and amino alcohols. Typically, minimum racemization occurs. This synthesis is accomplished in two steps, without separation of intermediate mixed carbonic anhydrides. The following sequence illustrates production of N-carbobenzoxy-L-prolyl-L-leucinol from commercially available N-carbobenzoxy-L-proline (Z-L-proline) and commercially available L-leucinol.

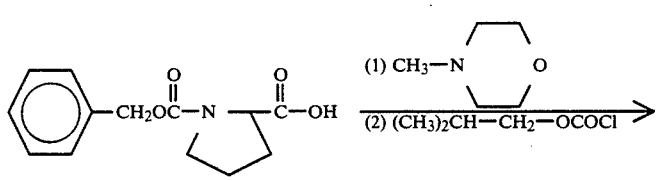

I

-continued

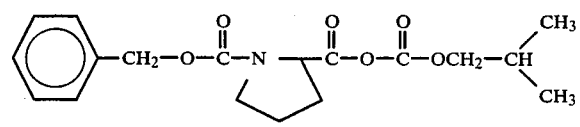

II

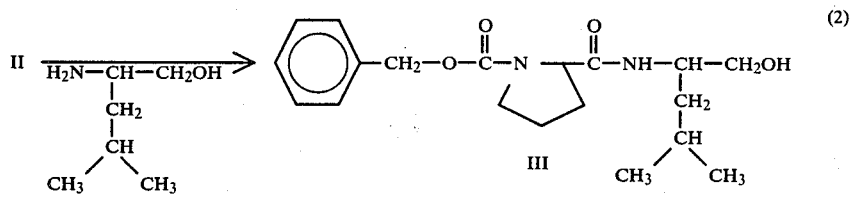

(2)

N-carbobenzoxy-L-proline (I), is reacted in approximately equimolar ratios with a base, for example, a tertiary amine, and a mixed acid chloride/ester to produce an intermediate mixed carbonic anhydride (II). N-methylmorpholine, a hindered tertiary amine, is a convenient base for this reaction. Other suitable bases include triethylamine and N,N'-dimethylpiperazine.

Isobutyl chloroformate can be employed as the mixed acid chloride/ester component. Other suitable mixed acid chloride/esters include methyl and cyclopropyl chloroformates. Tetrahydrofuran is a preferred solvent, and other inert, aprotic solvents, e.g., ethyl acetate, acetonitrile and 1,2-dimethoxyethane can also be employed. Reaction of the intermediate mixed anhydride (II) with L-leucinol in an approximately equimolar ratio provides N-carbobenzoxy-L-prolyl-L-leucinol (III).

Substitution of N-carbobenzoxy-L-γ-thiaproline, (prepared by reaction of 1-thiazolidine-4-carboxylic acid wit benzyl chloroformate) N-carbobenzoxy-L-γ-oxaproline, or other analogs of N-carbobenzoxy-L-proline as starting materials in the foregoing reaction sequence permits synthesis of other compounds of the invention. Similarly, other amino alcohols, e.g., L-valinol or L-homoalaninol, can be substituted for L-leucinol to provide other compounds of the invention. Reaction temperatures for this process are maintained from about −20° C. to about 0° C.

2. Active Ester Synthesis

This two step process employs N-carbobenzoxy-L-proline (I) and its analogs as starting materials, which are reacted in approximately equimolar ratios with hydroxy compounds, for example, o-nitrophenol, p-nitrophenol, trichlorophenol, or N-hydroxysuccinimide to produce highly reactive esters as intermediates (II). The following sequence illustrates preparation of N-carbobenzoxy-L-prolyl-L-leucinol (III), by reaction of approximately equimolar quantities of L-leucinol with an N-hydroxysuccinimide ester (II) of Z-L-proline (I). Dicyclohexylcarbodiimide (A) is conveniently employed to activate the starting acid, and is subsequently converted to dicyclohexylurea (B), a by-product which can be recovered by filtration.

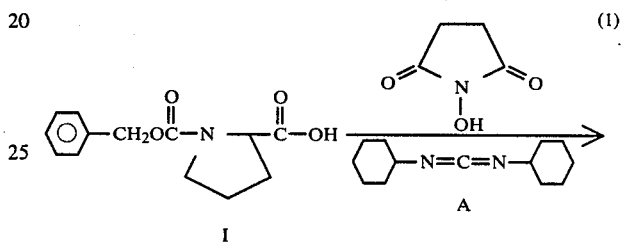

In similar fashion to the mixed anhydride synthesis previously described, other carbobenzoxy amino derivatives and other amino alcohols can be substituted in the active ester synthesis to provide related compounds of the invention. Suitable reaction temperatures for the active ester synthesis are from about 0° C. to about 40° C. Suitable solvents include 1,2-dimethoxyethane, N,N-dimethylformamide, or partially aqueous mixtures of organic solvents, such as aqueous methanolic dimethoxyethane.

3. Synthesis with Condensing Agents

Various condensing agents such as carbodiimides, N-ethyl-5-phenylisoxazolium-3'-sulfonate (Woodwards Reagent K) or carbonyldiimidazole can be used to form a peptide bond between a protected amino acid derivative e.g., N-carbobenzoxy-L-proline, and an amino alcohol, e.g., L-valinol, L-leucinol, or L-homoalaninol. By-products of this reaction can be removed by filtration (in the case of dicyclohexylcarbodiimide) or by water washing (in the cases of water-soluble reaction products of carbodiimides, Woodwards Reagent K, or carbonyldiimidazole.)

The condensing agent selected is reacted in an approximately equimolar ratio with the amino acid derivative at a reaction temperature from about 0° C. to about 40° C., forming a reactive, usually soluble, intermediate, which rapidly reacts with the amino alcohol to produce a compound of the invention. The following sequence illustrates reaction of dicyclohexylcarbodiimide (A) with Z-L-proline (I) and L-leucinol to provide N-carbobenzoxy-L-prolyl-L-leucinol (III) and dicyclohexylurea (B) as a by-product.

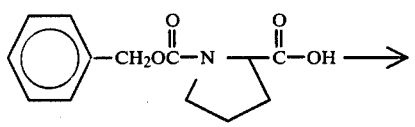

I

+

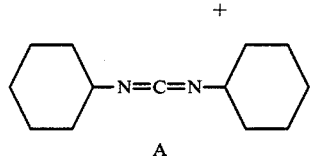

A

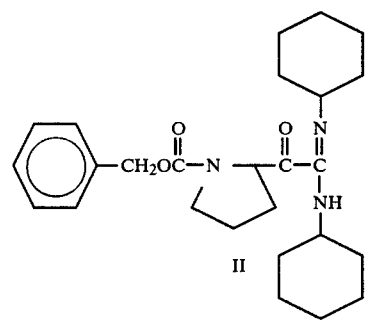

II

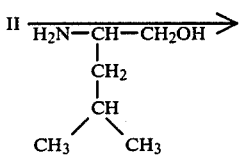
(2)

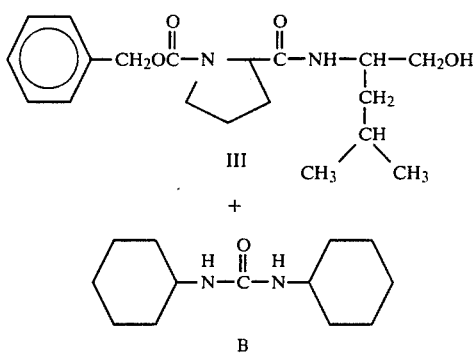

III

+

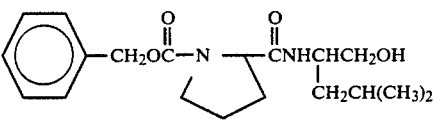

B

However, side reactions and rearrangement of intermediate species in this synthesis can complicate product purifications and reduce yields.

Mixtures of racemates obtained by the foregoing synthesis can be separated into stereoisomeric pure racemates (diasteroisomers) by various physical processes known in the art, e.g. chromatography or fractional distillation. Pure racemates can be separated into optical antipodes by conventional methods, for example, reaction with an optically active acid to form an ester, followed by separation by such physical means as fractional crystallization or chromatography.

The following examples illustrate various embodiments of the invention, and are not intended to limit the scope of the invention. In the examples, all parts and percentages are by weight, and all temperatures are in degrees Celsius unless otherwise indicated.

EXAMPLES

Example 1

Preparation of N-Carbobenzoxy-L-prolyl-L-leucinol

A solution containing 2.49 g (10 mmol) N-carbobenzoxy-L-proline and 1.01 g (10 mmol) N-methylmorpholine in approximately 100 ml tetrahydrofuran (THF) was cooled to −20° under nitrogen, and 1.37 g (10 mmol) isobutyl chloroformate was added with magnetic stirring. After five minutes, a solution of 1.17 g (10 mmol) L-leucinol in 5 mL THF was added, and the resulting reaction mixture was stirred for 30 minutes at 0°. THF evaporated under vacuum, and 30 mL water and 100 mL ethyl acetate were added to the resulting residue. After separation of aqueous and organic layers, the organic layer was decanted and retained. The aqueous layer was extracted with a second aliquot (100 mL) of ethyl acetate, and the resulting organic phase was separated. The combined organic layers were washed with 50 mL of ice-cold, 5% aqueous citric acid, followed by 50 mL of an ice-cold, 5% sodium bicarbonate solution. An organic phase was separated, dried over anhydrous magnesium sulfate, and the ethyl acetate was evaporated to provide 3.25 g of crude product. Recrystallization from a mixture of 40 mL ethyl acetate and 25 mL n-hexane gave 2.03 g (5.8 mmol; 58%) of colorless N- carbobenzoxy-L-prolyl-L-leucinol, m.p. 95°-95.5°, α²⁵D-72°, (C=1.03 g/100 mL acetone).

Anal: Calcd. for C₁₉H₂₈N₂O₄: C, 65.49; H, 8.10; N, 8.04. Found: C, 65.26; H, 8.01; H, 8.05.

Example 2

Preparation of N-Carbobenzoxy-L-prolyl-L-valinol

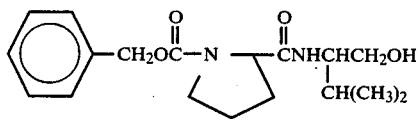

4.98 g (20 mmol) N-carbobenzoxy-L-proline, 2.73 g (20 mmol) isobutyl chloroformate, 2.02 g (20 mmol) N-methylmorpholine, and 2.73 g (26.5 mmol) L-valinol were contacted and reacted in THF, using a mixed anhydride procedure substantially as described in Example 1. The crude product, 5.93 g, was recrystallized from a mixture of 150 mL ethyl acetate and 250 mL n-hexane to give 5.24 g (15.7 mmol, 78%) of colorless N-carbobenzoxy-L-prolyl-L-valinol, m.p. 109.3°-110.7°, α²⁵D −65.3°, (C=1.01 g/100 mL in acetone).

Anal: Calcd. for C₁₈H₂₆N₂O₄: C, 64.65; H, 7.84; N, 8.38. Found: C, 64.82; H, 7.74; N, 8.24.

Example 3

Preparation of N-Carbobenzoxy-L-prolyl-L-valinol (active ester synthesis)

N-Carbobenzoxy-L-proline N-hydroxysuccinimide ester (3.45 g; 10 mmol) was dissolved in 75 mL 1,2-dimethoxyethane, to which 1.03 g (10 mmol) L-valinol and 1.01 g (10 mmol) triethylamine were added. The resulting mixture was stirred overnight at 25°, and solvent was evaporated. The resulting residue was dissolved in ethyl acetate, and this solution was washed with water, 5% citric acid, and 5% sodium bicarbonate, and dried over magnesium sulfate. Ethyl acetate was evaporated, providing 3.01 g of crude, solid N-carbobenzoxy-L-prolyl-L-valinol. Recrystallization from a mixture of 28 mL ethyl acetate and 8 mL n-hexane gave 2.26 g of a white crystalline modification, m.p. 111°-112.5°, α²⁵D −68.2° (C=1.0 g/100 mL in acetone). An infrared spectrum obtained for this product was significantly different from that corresponding to the material described in Example 2. However, following a second crystallization, an infrared spectrum of the resulting product agreed with that of the product obtained in Example 2.

Example 4

Preparation of N-Carbobenzoxy-L-prolyl-(β-hydroxyethyl)amide

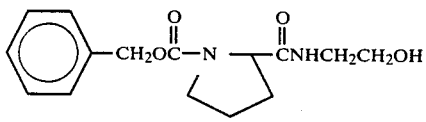

4.98 g (20 mmol) N-carbobenzoxy-L-proline, 2.73 (20 mmol) isobutyl chloroformate, 2.02 g (20 mmol) N-methylmorpholine, and 1.22 g (20 mmol) β-ethanolamine were contacted and reacted in THF substantially according to the mixed anhyride procedure described in Example 1. The resulting crude product, 4.06 g, was recrystallized from a mixture of 40 mL ethyl acetate and 25 mL n-hexane, providing 3.22 g (11.0 mmol, 55%) of white, solid N-carbobenzoxy-L-prolyl-(β-hydroxethyl)amide, m.p. 99.4°-99.9°, α²⁵D −45.4°, (C=1.01 g/100 mL in acetone).

| Anal: | | Calcd. for C₁₅H₂₀N₂O₄: | | |
|---|---|---|---|---|
| | C, | 61.63; | H, 6.90; | N, 9.58. |
| Found: | C, | 61.65; | H, 6.79; | N, 9.39. |
| | | 61.60 | 6.80 | 9.38. |

Example 5

Preparation of N-Carbobenzoxy-L-prolyl-L-alaninol

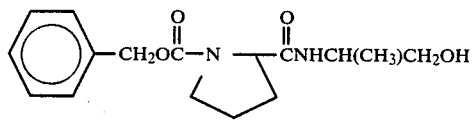

4.98 g (20 mmol) N-carbobenzoxy-L-proline, 2.73 g (20 mmol) isobutyl chloroformate, 2.02 g (20 mmol) N-methylmorpholine, and 1.50 g (20 mmol) L-alaninol were contacted and reacted in THF substantially according to the mixed anhydride procedure described in Example 1. Recrystallization of crude product from 50 ml ehtyl acetate provided 3.61 g (11.8 mmol, 59%) of colorless, crystalline N-carbobenzoxy-L-prolyl-L-alaninol; m.p. 126.5°-127.6°, α²⁵D−48.9° (C=1.03 g/100 mL in acetone).

| Anal: | | Calcd. for C₁₆H₂₂N₂O₄: | | |
|---|---|---|---|---|
| | C, | 62.72; | H, 7.24; | N, 9.14. |
| Found: | C, | 63.04; | H, 7.21; | N, 9.30 |
| | | 62.76 | 7.21 | 9.33. |

Example 6

Preparation of N-Carbobenzoxy-L-prolyl-L-homoalaninol

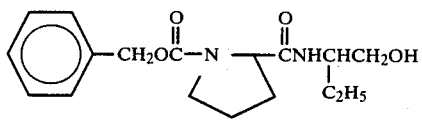

This compound was prepared from 4.99 g (20 mmol) N-carbobenzoxy-L-proline, 2.73 g (20 mmol) isobutyl chloroformate, 2.02 g (20 mmol) N-methylmorpholine, and 1.78 g (20 mmol) d-(+)2-amino-1-butanol, substantially according to the mixed anhydride procedure described in Example 1. Crude product (5.16 g) was recrystallized from a mixture of 60 mL ethyl acetate and 15 mL n-hexane to give 4.18 g (13 mmol, 65%) of colorless, crystalline N-carbobenzoxy-L-prolyl-L-homoalaninol; m.p. 105.4°-106.3°, α²⁵D −69.7 (C=1.04 g/100 mL in acetone). A stereochemical assignment for this product was based upon observed similarity of specific rotation to specific rotations measured for L-L isomers of carbobenzoxy-prolyl-leucinol (Example 1), carbobenzoxy-prolyl-valinol (Example 2) and carbobenzoxy-prolyl-alaninol (Example 5).

Anal:  Calcd. for C₁₇H₂₄N₂O₄:

| | | | | | | | |
|---|---|---|---|---|---|---|---|
| | C, | 63.73; | H, | 7.55; | N, | 8.74. | |
| Found: | C, | 64.03; | H, | 7.49; | N, | 8.91 | |
| | | 63.78 | | 7.54 | | 8.94. | |

Example 7

Preparation of
N-Carbobenzoxy-L-prolyl-D-homoalaninol

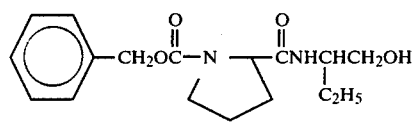

4.98 g (20 mmol) N-carbobenzoxy-L-proline, 2.73 g (20 mmol) isobutyl chloroformate, 2.03 g (20 mmol) N-methylmorpholine, and 1.78 g (20 mmol) 1-(-)-2-amino-1-butanol were contacted and reacted in THF substantially according to the mixed anhydride procedure described in Example 1. The resulting crude product, 5.58 g, was recrystallized from a mixture of 40 mL ethyl acetate and 60 mL n-hexane, providing 3.87 g (12.1 mmol, 60.4%) of colorless crystalline N-carbobenzoxy-L-prolyl-D-homoalaninol; m.p. 99.5°–101.5°, $\alpha^{25}D-28.5°$ (C=1.00 g/100 mL of acetone).

Anal: Calcd. for $C_{17}H_{24}N_2O_4$: C, 63.73; H, 7.55; N, 8.74. Found: C, 63,96; H, 7.44; N, 8.69.
Stereochemical assignment was based upon observed similarity of specific rotation to that determined for N-carbobenzoxy-L-prolyl-D-valinol (Example 8 below).

Example 8

Preparation of N-Carbobenzoxy-L-prolyl-D-Valinol

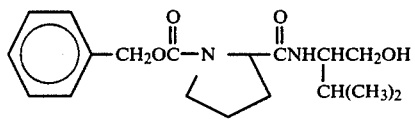

N-Carbobenzoxy-L-prolyl-DL-valinol was prepared by reacting 9.97 g (40 mmol) N-carbobenzoxy-L-proline, 5.46 g (40 mmol) isobutyl chloroformate, 4.05 g (40 mmol) N-methylmorpholine, and 4.13 g (40 mmol) DL-valinol substantially according to the mixed anhydride procedure described in Example 1. A portion, 1.00 g, of crude product was dissolved in 120 mL ethyl acetate, and 80 mL n-hexane were added. This solution was stirred vigorously and seeded with a crystal of N-carbobenzoxy-L-prolyl-L-valinol. After 5 minutes, crystalline product (100 mg) was separated by filtration. High performance liquid chromatography (HPLC) indicated that the product contained 76% N-carbobenzoxy-L-prolyl-D-valinol (L-D isomer) and 24% N-carbobenzoxy-L-prolyl-L-valinol (L-L isomer). HPLC analysis was conducted using a 4.6 mm ID×25 cm column packed with 5–6 μm diameter particles of porous silica, and a linear gradient (3→100% B in 30 minutes), using 1-chlorobutane as solvent A and 1:1 methanol/acetonitrile as solvent B. A first peak (11.2 minutes) was the desired L-D isomer, and a second peak (11.6 minutes) was the L-L isomer, characterized in Example 2 above. HPLC separation was repeated with a series of 5 mg injections to give a total of 64 mg (0.19 mmol) pure N-carbobenzoxy-L-prolyl-D-valinol. This product could also be isolated directly from the crude reaction product by a series of fractional crystallizations from ethyl acetate/n-hexane, then ethanol/n-hexane. Pure N-carbobenzoxy-L-prolyl-D-valinol melted at 118.0°–118.2°, $\alpha^{25}D-27.6°$, (C=1.01 g/100 mL in acetone).

Example 9

Preparation of N-Carbobenzoxy-D-prolyl-L-valinol

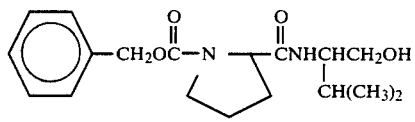

2.49 g (10 mmol) N-carbobenzoxy-D-proline, 1.37 g (10 mmol) isobutyl chloroformate, 1.01 g (10 mmol) N-methylmorpholine, and 1.03 g (10 mmol) L-valinol were contacted and reacted in THF substantially according to the procedure described in Example 1. Crude product (2.82 g) was recrystallized from a mixture of 20 mL ethyl acetate and 15 mL n-hexane, to give 2.37 g (7.1 mmol, 71%) of colorless crystalline N-carbobenzoxy-D-prolyl-L-valinol; m.p. 117.5°–118.6°, $\alpha^{25}D=+26.7°$ (C=1.02 g/100 mL in acetone).

| Anal: | | Calcd. for $C_{18}H_{26}N_2O_4$: | | | | |
|---|---|---|---|---|---|---|
| | C, | 64.65; | H, | 7.84; | N, | 8.38. |
| Found: | C, | 64.69; | H, | 7.73; | N, | 8.45 |
| | | 64.68 | | 7.74 | | 8.37. |

Example 10

Preparation of N-Carbobenzoxy-D-prolyl-D-valinol

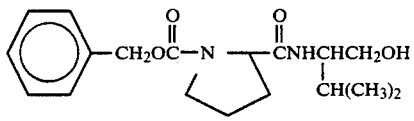

4.98 g (20 mmol) N-carbobenzoxy-D-proline, 2.73 g (20 mmol) isobutyl chloroformate, 2.02 g (20 mmol) N-methylmorpholine, and 2.73 g (26.5 mmol) DL-valinol were contacted and reacted in THF substantially according to the mixed anhydride procedure described in Example 1. The resulting crude product, 7.23 g, was dissolved in 25 mL hot ethyl acetate, and 25 mL n-hexane were added. The resulting solution was filtered, seeded with a crystal of N-carbobenzoxy-D-prolyl-D-valinol, and allowed to stand for one hour. The resulting crystalline product of the undesired DL isomer was separated, and the solvent was evaporated from the filtrate. The residue was dissolved in 5 mL hot ethanol, to which 50 mL cold n-hexane were added. After filtration, 750 ml additional n-hexane were added to the filtrate, the resulting solution seeded, and crystalline product D-D was separated. This ethanol/n-hexane recrystallization step was repeated with the D-D crude product to provide 330 mg (0.99 mmol, 5%) N-carbobenzoxy-D-prolyl-D-valinol (D-D isomer), m.p. 113°–114°, $\alpha^{25}D+67.6°$ (C=1.0 g/100 mL in acetone).

Anal: Calcd. for $C_{18}H_{26}N_2O_4$: C, 64.65; H, 7.84; N, 8.38. Found: C, 65.07; H, 7.58; N, 8.49.

Example 11

Preparation of N-Carbobenzoxy-L-γ-thiaprolyl-L-valinol

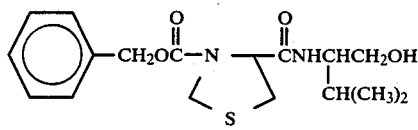

A stirred solution of 18.17 g (136 mmol) 1-thiazolidine-4-carboxylic acid in 136 mL 1.0 N sodium hydroxide solution, cooled in an ice bath, was treated simultaneously with 25.52 g (149 mmol) benzyl chloroformate and 50 mL 1.0 N sodium hydroxide solution. Following evaporation of volatiles, the resulting aqueous solution was washed twice with diethyl ether and the resulting ether extracts discarded.

The remaining aqueous solution was acidified to pH 2, extracted twice with ethyl acetate, and the combined extracts dried over anhydrous magnesium sulfate. Ethyl acetate was evaporated, providing a colorless oil which crystallized on standing. A 2.39 g (10 mmol) portion of this material (N-carbobenzoxy-L-γ-thiaproline), 1.37 g (10 mmol) isobutyl chloroformate, 1.01 g (10 mmol) N-methylmorpholine, and 1.03 g (10 mmol) L-valinol were reacted substantially according to the mixed anhydride procedure described in Example 1. The resulting crude oily product crystallized on standing. Recrystallization from a mixture of 25 mL ethyl acetate and 60 mL n-hexane gave 1.22 g (3.5 mmol, 35%) N-carbobenzoxy-L-γ-thiaprolyl-L-valinol, m.p. 92°–94°, $\alpha^{25}D - 123.7°$ (C=1.00 g/100 mL in acetone).

Anal: Calcd. for $C_{17}H_{24}N_2O_4S$: C, 57.93; H, 6.86; N, 7.95. Found: C, 57.75; H, 6.71; N, 7.95.

Example 12

Preparation of N-Carbobenzoxy-L-γ-oxaprolyl-L-valinol

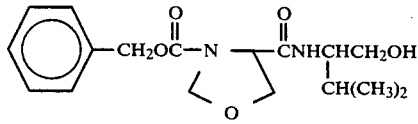

3-Carbobenzoxyoxazolidine-4S-carboxylic acid was prepared by the following condensation procedure, which is substantially similar to that described by Wolfe et al., *Tetrahedron Letters*, pp. 3913–3916 (1979). A mixture of L-serine (10.51 g, 0.10 mol), 2 N NaOH (48 mL, 0.12 mol) and 37% formaldehyde (8.1 mL, 0.10 mol) was stirred at 5° overnight, then treated with benzyl chloroformate (17.05 g, 0.10 mol) in acetone (40 mL), while maintaining the pH of the solution above 7 by adding solid sodium bicarbonate. The resulting mixture was diluted with water (100 mL) and extracted with two 50 mL aliquots of diethyl ether. The extracts were discarded, and the remaining aqueous layer acidified with hydrochloric acid and reextracted with three 100 mL aliquots of diethyl ether.

The resulting ether extracts were dried over anhydrous magnesium sulfate and evaporated at 40°/0.1 mm, providing 21.2 g (84.4 mmol, 84%) product in the form of a colorless syrup, which solidified to a colorless solid upon prolonged standing. This was pure material; attempts to distill it using a Kugelrohr apparatus resulted in decomposition. 3-Carbobenzoxyoxazolidine-4S-carboxylic acid has $\nu_{max}^{CHCl_3}$ 3010, 2950, 2880, 1720, 1705 cm$^{-1}$; $\lambda_{max}^{EtOH}$ 273 ($\epsilon$120), 268 ($\epsilon$185), 263 ($\epsilon$220) and 257 nm ($\epsilon$170); $[\alpha]_D^{25} -60.8 \pm 0.5°$, $-62.3 + 0.5°$, (C 1.01, 1.02 EtOH); pKa 4.35, 4.30; $^1$H NMR (CDCl$_3$/TMSi), δ 10.39 (s) CO$_2$H, 7.17 (s) C$_6$H$_5$, 5.03 (s) OCH$_2$Ar, 4.83 (s) NCH$_2$O, 4.39 (t, J=6) NCHCO$_2$H and 4.03 ppm (d, J=6), OCH$_2$.

| Anal: | | Calcd. for $C_{12}H_{13}NO_5$: | | | | | |
|---|---|---|---|---|---|---|---|
| | C, | 57.37; | H, | 5.22; | N, | 5.58. | |
| Found: | C, | 56.97; | H, | 5.21; | N, | 5.48 | |
| | | 57.05 | | 5.21 | | 5.51. | |

N-Carbobenzoxy-L-γ-oxaprolyl-L-valinol was prepared from 5.02 g (20 mmol) 3-carbobenzoxyoxazolidine-4S-carboxylic acid, 2.73 g (20 mmol) isobutyl chloroformate, 2.02 g (20 mmol) N-methylmorpholine, and 2.06 g (20 mmol) L-valinol substantially according to the mixed anhydride procedure described in Example 1. Crude product (7.08 g) was recrystallized from a mixture of 75 mL ethyl acetate and 225 mL n-hexane to give 4.93 g (14.7 mmol; 73%) of colorless crystalline N-carbobenzoxy-L-γ-oxaprolyl-L-valinol, m.p. 118°–119.5°, $\alpha^{25}D - 82.6°$ (C=1.06 g/100 mL in acetone).

Anal: Calcd. for $C_{17}H_{24}N_2O_5$: C, 60.70; H, 7.19; N, 8.33. Found: C, 60.73; H, 7.13; N, 8.27.

Example 13

Preparation of N-Carbobenzoxy-5R-methyloxazolidine-4S-carbonyl-L-valinol

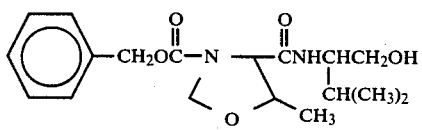

3-Carbobenzoxy-5R-methyloxazolidine-4S-carboxylic acid was prepared substantially according to the Wolfe et al. condensation procedure described in Example 12, except that L-serine was replaced with 0.20 mol of L-threonine. The resulting product was obtained as a colorless syrup, 36.07 g (0.136 mol, 68%). Attempts to distill this material at 160°/0.1 mm in a Kugelrohr apparatus were accompanied by some decomposition. 3-carbobenzoxy-5R-methyloxazolidine-4S-carboxylic acid has $\nu_{max}^{CHCl_3}$ 3600, 3000, 2860, 1700 cm$^{-1}$; $\lambda_{max}^{EtOH}$ 267 ($\epsilon$ 470), 263 ($\epsilon$ 570), 257 ($\epsilon$ 640) and 252 nm ($\epsilon$ 550); $[\alpha]_D^{25} - 72.8 \pm 0.5°$, (C 1.02 EtOH); pKa 4.65, 4.60; $^1$H NMR (CDCl$_3$/TMSi), δ 8.42 (b) CO$_2$H, 7.19 (s) C$_6$H$_5$, 5.02 (s) OCH$_2$Ar, 4.85 (AB each member d, J=4.5), NCH$_2$O, 4.14 (quintet, J=6) OCH, 3.88 (d, J=6) NCHCO$_2$H, and 1.37 ppm (d, J=6 ) CH$_3$.

| Anal: | | Calcd. for $C_{13}H_{15}NO_5$: | | | | | |
|---|---|---|---|---|---|---|---|
| | C, | 58.86; | H, | 5.70; | N, | 5.28. | |
| Found: | C, | 60.15; | H, | 5.77; | N, | 4.94 | |
| | | 60.04 | | 5.78 | | 5.01. | |

N-Carbobenzoxy-5R-methyloxazolidine-4S-carbonyl-L-valinol was prepared from 5.30 g (20 mmol) 3-carbobenzoxy-5R-methyloxazolidine-4S-carboxylic acid, 2.73 g (20 mmol) isobutyl chloroformate, 2.02 g (20 mmol) of N-methylmorpholine, and 2.06 g (20 mmol) L-valinol, substantially according to the mixed anhydride procedure described in Example 1. Crude product (6.98 g) was recrystallized from a mixture of 75 mL ethyl acetate and 225 mL n-hexane to give 4.93 g (70%) of colorless crystalline N-carbobenzoxy-5R-methyloxazolidine-4S-carbonyl-L-valinol, m.p. 98°–101°, $\alpha^{25}D$ −75.3° (C=1.00 g/100 mL in acetone).

Anal: Calcd. for $C_{18}H_{26}N_2O_5$: C, 61.70; H, 7.48; N, 8.00. Found: C, 61.78; H, 7.39; N, 7.94.

Example 14

Preparation of N-Carbobenzoxy-D-γ-oxaprolyl-L-valinol

3-Carbobenzoxyoxazolidine-4R-carboxylic acid was prepared substantially according to the Wolfe et al. condensation procedure described in Example 12, except that L-serine was replaced with 0.20 mol of D-serine. The resulting product was obtained as a colorless syrup, 37.55 g (0.15 mol, 75%) which slowly crystallized to a colorless solid on standing. 3-Carbobenzoxy oxazolidine-4R-carboxylic acid has $\nu_{max}^{CHCl_3}$ 3025, 3015, 2980, 2885, 1715 cm$^{-1}$; $\lambda_{max}^{ETOH}$ 268 (ε 118), 264 (ε 186), 258 (ε 226) and 252 nm (ε 176); $[\alpha]_D^{25}$ +60.7 ±0.5°, (C 1.01 EtOH); pKa 3.80, 3.90; $^1$H NMR (CDCl$_3$/TMSi), δ10.22 (s) CO$_2$H, 7.17 (s) C$_6$H$_5$, 5.02 (s) OCH$_2$Ar, 4.83 (s) NCH$_2$O, 4.39 (t, J=5) NCHCO$_2$H and 4.03 (d, J=5) OCH$_2$.

| Anal: | | Calcd. for $C_{12}H_{13}NO_5$: | | | | | |
|---|---|---|---|---|---|---|---|
| | C, | 57.37; | H, | 5.22; | N, | 5.58. | |
| Found: | C, | 56.98; | H, | 5.19; | N, | 5.39 | |
| | | 56.96 | | 5.23 | | 5.33. | |

N-Carbobenzoxy-D-γ-oxaprolyl-L-valinol was prepared from 5.02 g (20 mmol) 3-carbobenzoxyoxazolidine-4R-carboxylic acid, 2.73 g (20 mmol) isobutyl chloroformate, 2.02 g (20 mmol) N-methylmorpholine, and 2.06 g (20 mmol) L-valinol, substantially according to the mixed anhydride procedure described in Example 1. Crude product was recrystallized from a mixture of 25 L ethyl acetate and 75 mL n-hexane to give 4.53 g (13.5 mmol; 67%) of white crystalline N-carbobenzoxy-D-γ-oxaprolyl-L-valinol, m.p. 139.5–141.7°, $\alpha^{25}D$ +55.4° (C=1.01 g/100 mL in acetone).

| Anal: | | Calcd. for $C_{17}H_{24}N_2O_5$: | | | | | |
|---|---|---|---|---|---|---|---|
| | C, | 60.70; | H, | 7.19; | N, | 8.33. | |
| Found: | C, | 60.70; | H, | 6,94; | N, | 8.18 | |
| | | 60.63 | | 6.97 | | 8.55. | |

Example 15

Preparation on N-(4-Fluorobenzyloxycarbonyl)-L-prolyl-L-valinol

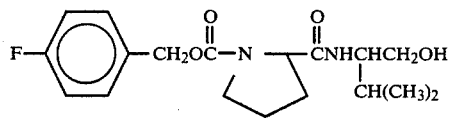

Preparation of p-fluorobenzyl p-nitrophenyl carbonate was carried out by the following procedure. To an ice-cold solution of 13.87 g (110 mmol) p-fluorobenzyl alcohol and 7.90 g (100 mmol) pyridine in 80 mL acetone was added 20.3 g (100 mmol) p-nitrophenyl chloroformate in small portions. The resulting mixture was stirred for 15 minutes and poured into 500 mL water. The solid precipitate was collected, washed with water, and dried to give 23.7 g of crude product. Recrystallization from a mixture of 150 mL ethyl acetate and 450 mL n-hexane gave 16.4 g (56 mmol, 56%) of white crystalline p-fluorobenzyl p-nitrophenyl carbonate, m.p. 135.0–136.5°. An nmr spectrum obtained for this material was in agreement with the proposed structure, but the presence of an impurity was indicated.

Preparation of p-fluorobenzyloxycarbonyl-L-proline was carried out by the following procedure. A solution of 8.14 g (71 mmol) L-proline in 35 mL cold 2.00 N sodium hydroxide was added to a solution of 20.6 g (71 mmol) p-fluorobenzyl p-nitrophenyl carbonate in 150 ml THF. An additional 35 mL-portion of 2.00 N sodium hydroxide was added, and the resulting solution was stirred overnight at room temperature. THF was evaporated under reduced pressure, and the residual aqueous solution was adjusted to pH 5.8 with 1N hydrochloric acid. The aqueous solution was extracted three times with diethyl ether to remove p-nitrophenol and unreacted starting materials. The aqueous solution was separated, adjusted to pH 2 with hydrochloric acid, and extracted twice with diethyl ether. The ether extracts were combined, washed with water, then with saturated sodium chloride solution, and finally dried over magnesium sulfate. Organic solvent was evaporated to leave 16.1 g of yellow, oily p-fluorobenzyloxycarbonyl-L-proline.

N-(4-fluorobenzyloxycarbonyl)-L-prolyl-L-valinol was prepared from 16.1 g (60.2 mmol) p-fluorobenzyloxycarbonyl-L-proline, 8.22 g (60.2 mmol) isobutyl chloroformate, 6.09 g (60.2 mmol) N-methylmorpholine, and 6.21 g (60.2 mmol) L-valinol, substantially according to the mixed anhydride procedure described in Example 1. The resulting crude product (19.46 g) was recrystallized from a mixture of 100 mL ethyl acetate and 200 mL n-hexane to give 16.69 g (47.4 mmol, 78.7%) of N-(4-fluorobenzyloxycarbonyl)-L-prolyl-L-valinol, m.p. 123°–124°. $\alpha_D^{25}$ −60.2° (C=1.02 g/100 mL in acetone). An nmr obtained for this material spectrum verified the assigned structure: $^1$H NMR (CDCl$_3$/TMSi), 220 mc, δ0.85, m, 6H (valinol CH$_3$); δ1.9, m, 2H (proline γ-CH$_2$); δ2.2, m, 3H (valinol β-CH and proline β-CH$_2$); δ 3.35, m, 3H (proline δCH$_2$); δ 3.58, m, 2H (CH$_2$OH); δ 4.34, m, H (valinol α-CH); δ 5.0, s, 2H (benzyl CH$_2$); δ 6.30–6.80, m, H (NH); δ 7.03, m, 2H (aromatic); δ 7.35, m, 2H (aromatic).

| Anal: | | Calcd. for $C_{18}H_{25}FN_2O_4$: | | | | |
|---|---|---|---|---|---|---|
| | C, | 61.36; | H, | 7.15; | N, | 7.95. |
| Found: | C, | 61.87; | H, | 7.12; | N, | 8.26 |
| | | 61.48 | | 7.17 | | 8.12. |

Example 16

Preparation of N-(p-Chlorobenzyloxycarbonyl)-L-prolyl-L-valinol

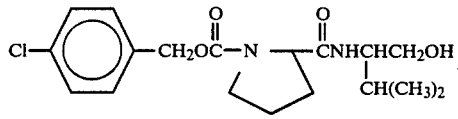

Preparation of p-chlorobenzyl p-nitrophenyl carbonate was carried out by contacting and reacting 9.0 g (63 mmol) p-chlorobenzyl alcohol, 4.74 g (60 mmol) pyridine, and 12.2 g (60 mmol) p-nitrophenyl chloroformate, substantially according to the procedure described in Example 15 for preparation of the corresponding p-fluoro compound. Product obtained after purification by recrystallization melted at 138.5°–140.5°, $\alpha^{25}D$ −54.2° (C=1.04 g/100 mL in acetone).

Preparation of p-chlorobenzyloxycarbonyl-L-proline was carried out starting with 5.2 g (17 mmol) p-chlorobenzyl p-nitrophenyl carbonate and 1.96 g (17 mmol) L-proline, substantially according to the procedure described in Example 15 for preparation of the corresponding p-fluoro compound. A total of 3.78 g of yellow, oily product was obtained. An nmr spectrum was in agreement with the structure.

The subject compound was prepared from 0.85 g (2.98 mmol) p-chlorobenzyloxycarbonyl-L-proline, 0.41 g (2.98 mmol) isobutyl chloroformate, 0.30 g (2.97 mmol) N-methylmorpholine, and 0.31 g (2.98 mmol) L-valinol, substantially according to the mixed anhydride procedure described in Example 1. N-(p-chlorobenzyloxycarbonyl)-L-prolyl-L-valinol obtained after recrystallization from ethyl acetate/n-hexane melted at 143°–144.5°.

Anal: Calcd. for $C_{18}H_{25}ClN_2O_4$: C, 58.61; H, 6.83; N, 7.60. Found: C, 58.90; H, 6.33; N, 7.46.

Example 17

Preparation of N-(p-Methylbenzyloxycarbonyl)-L-prolyl-L-valinol

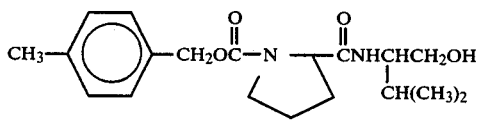

Preparation of methylbenzyl p-nitrophenyl carbonate was carried out starting with 12.2 g (100 mmol) p-methylbenzyl alcohol, 7.9 g (100 mmol) pyridine, and 20.6 g (101 mmol) p-nitrophenyl chloroformate, substantially according to the procedure described in Example 15 for preparation of the corresponding p-fluoro compound. A total of 16.1 g (55 mmol, 55%), of product was obtained as a hemihydrate after recrystallization, m.p. 90°–93.5°. An nmr spectrum obtained for this product was in agreement with its proposed structure.

Preparation of p-methylbenzyloxycarbonyl-L-proline was carried out starting with 5.74 g (19.4 mmol) p-methylbenzyl p-nitrophenyl carbonate hemihydrate and 2.03 g (17.7 mmol) L-proline, using a procedure substantially similar to that described in Example 15 for preparation of the corresponding p-fluoro compound. A total of 4.0 g (13.6 mmol, 77%) of light yellow, oily product was obtained. An nmr spectrum was in agreement with the structure.

The subject compound was prepared from 3.9 g (14.8 mmol) p-methylbenzyloxycarbonyl-L-proline, 2.0 g (14.6 mmol) isobutyl chloroformate, 1.5 g (14.8 mmol) N-methylmorpholine, and 1.5 g (14.5 mmol) L-valinol, using a procedure described in Example 1. The product, N-(p-methylbenzyloxycarbonyl)-L-prolyl-L-valinol, obtained after recrystallization from ethyl acetate/ n-hexane, melted at 122°–123.5°, $\alpha^{25}D$ −61.9° (C=1.00 g/100 mL in acetone).

| Anal: | | Calcd. for $C_{19}H_{28}N_2O_4$: | | | | |
|---|---|---|---|---|---|---|
| | C, | 65.49; | H, | 8.10; | N, | 8.04. |
| Found: | C, | 64.59; | H, | 7.88; | N, | 8.18 |
| | | 64.56 | | 7.99 | | 8.12. |

FORMULATIONS

Useful formulations of the compounds of the invention can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.01% to 99% be weight of active ingredient(s) and at least one of (a) about 0.1% to 20% surfactant(s) and (b) about 1% to 99.99% solid or liquid inert diluent(s).

Lower or higher levels of active ingredient can be present depending on intended use and physical properties of the selected compound. Higher ratios of surfactant to active ingredient are sometimes desirable, and are achieved by incorporation into the formulation or by tank mixing.

Various inert, solid diluents known in the art as useful agents for application of argricultural chemicals can be employed in combination with the compounds of the invention. These include kaolinite, bentonite, diatomaceous earth, attapulgite, and the like. More absorptive diluents are preferred for wettable powders and denser ones for dusts. Typical liquid diluents and solvents are described in Marsden, "Solvents Guide," 2nd ED., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

Methods of making such compositions are well known. Solutions are prepared by simply mixing the ingredients. Fine solid compositions are made by blending and, usually grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

UTILITY

The compounds of the invention selectively enhance uptake of nitrate and ammonium ions by plant roots, and plants treated with compounds of the invention exhibit an enhanced rate of growth. This effect could be useful in reducing fertilizer requirements of certain plant varieties, especially those which require large applications of nitrogen. The enhanced nutrient ion uptake effect has been demonstrated in laboratory tests and confirmed in selective greenhouse tests and field tests, which are described in detail below.

Rates of application for the compounds of the invention are determined by a number of factors, including crop species involved, weather and climate, formulations selected, mode of application, amount of foliage present, amount of available nitrogen in the soil prior to treatment, etc. In general terms, the subject compounds should be applied at levels of about 0.01 to 10 kg/ha, the lower rates being suggested for use on lighter soils and/or those having a low organic matter content, for selective application or for situations where only short-term enhancement of ion uptake is required. The compounds of the invention can be used in combination with one another or with suitable nitrogen-containing fertilizer compositions.

Evaluation of N-carbobenzoxy-L-prolyl-L-valinol (Example 2) at varying test concentrations indicated that a media concentration of about 50 ppm was optimal for stimulation of nitrate ion uptake by immersed corn root sections. In addition, nitrate ion uptake stimulation by test compounds was more pronounced when nitrate ion availability was low. This observation suggests that the compounds of the invention will provide increased yields in nitrate-deficient soils.

EXPERIMENTAL METHODS AND RESULTS

1. In-vitro Ion Uptake Tests Using Root Sections

Corn (Pioneer Hybrid 3320), wheat (Arther), sorghum (SC-599-6), barley (CM-721), rice (m101), and cotton (Tamcot SP-37) seeds were disinfected with a 1% sodium hypochlorite solution and placed in 20.3 cm×30.5 cm×5.1 cm Pyrex glass utility trays which were lined with 4 layers of bleached paper towels and irrigated with 150 mL of 0.2 mM CaCl$_2$ solution. The trays were covered with plastic food wrap, perforated to permit air exchange, and placed in a dark growth room which was maintained at 30° and 90% relative humidity. About 48 hours later, another 150 mL of 0.2 mM CaCl$_2$ solution was added to each tray to maintain water sauration of the paper towels.

Two centimeter root sections were cut 0.5 to 2.5 cm from the tip of 3-day-old etiolated seedling roots. Batches of 20 (for corn and cotton), or 40 (for wheat, barley and rice) root sections were tied in cheesecloth bags, leaving a 20–30 cm length of string to facilitate movement between test solutions. Root tissue was washed at 30±1° by immersing the cheesecloth bags in a well-aerated 0.2 mM K$_2$HPO$_4$/KH$_2$PO$_4$ solution, pH 6.0, for 4 hours. During the last 30 minutes of this washing period, 1 mM potassium nitrate solution was introduced to induce nitrate reductase activity. For uniformity, 100 mL washing solution was used for every bag of root sections (about 300 mg fresh tissue).

Nitrate ion uptake was measured using radioactive chlorate ion ($^{36}$ClO$_3^{\ominus}$) as a mimic for nitrate ion (Deane-Drummond et al., Plant Physiol. 70:50–54 (1982)). Uptake was measured by incubating 20 or 40 cheesecloth-bound washed root segments for 30 minutes in 100 mL absorption solution. The absorption solution contained 0.5 mM potassium nitrate, 0.2 mM calcium chloride, 5 mM MES buffer, and 5 mg/L sodium molybdate. This solution was adjusted to pH 6 with potassium hydroxide, and labeled with 10,000 cpm/ml of carrier-free radioactive chlorate ion. Absorption temperatures was maintained at 30±1° in a water bath, and moderate aeration was provided. All test compounds were added to the absorption solution. After the absorption period, the cheesecloth bag containing root sections was rinsed with distilled water for 10 seconds and then immersed in 100 mL of ice-cold, aerated 0.2 mM calcium chloride solution for 20 minutes to remove exchangeable components of absorbed $^{36}$ClO$_3^{\ominus}$. Root sections were then removed from the cheesecloth bags, blotted dry, placed in a preweighed scintillation vial, and weighed to determine fresh tissue weight. One mL water and 10 mL Scinti Verse I (Fisher Scientific Co.) scintillation fluid were added, and radioactivity determined by scintillation counting. The rate of nitrate ($^{36}$ClO$_3^{\ominus}$) uptake in micromols per gram fresh weight of tissue per hour was calculated.

Nitrate ion uptake into corn roots was also determined by homogenizing root segments previously exposed to the nitrate absorption solution (without added $^{36}$ClO$_3^{\ominus}$) with a precooled glass homogenizer in 5 mL of cold extraction medium. This medium contained 23 mM phosphate buffer pH 8.8, 5 mM cysteine, 2.5 mM EDTA, and 0.1% Neutronyx 600 (Onyx Chemical Co., Jersey City, N.J.). The resulting homogenate was centrifuged at 30,000 xg for 15 minutes, and an aliquot of the resulting supernatant solution reserved for nitrate ion determination, using an Orion nitrate ion specific electrode. The same tissue extract was used for nitrate reductase activity determination (below).

Ammonium ion uptake was determined by measuring the disappearance of ammonium ion from an uptake solution containing 1 mmol ammonium chloride, 0.2 mM calcium chloride and 5 mM MES buffer, pH 6.0, with an Orion ammonium ion-specific electrode. The extraction procedure was substantially similar to that described for nitrate ion uptake, above.

Nitrate reductase activity was determined using a modification of the procedure of Hageman and Huckles- by, Methods Enzymol. 23 (Part A), 491–503 (1971). A typical assay mixture contained 26 μmol potassium phosphate buffer, pH 7.5; 50 μmol potassium nitrate; 20 μmol nicotinamide adenine dinucleotide (reduced form) (NADH); 1.4 μmol EDTA; enzyme extract (tissue homogenate) and water, to make a final volume of 2 mL. The reaction was terminated by adding 0.2 mL 0.5 M zinc acetate plus 1.2 mL phenazine methosulfate (46 mg/l). After standing 20 minutes at room temperature, extracts were centrifuged at 1000 xg for 10 minutes. The resulting supernatant was used for determination of nitrite.

Experimental results obtained at a 50 ppm concentration of test compound are summarized in Table I, below. Test compounds are identified in Table I by Example number, and by the identity of substituents X, Y, Z and R in the following formula:

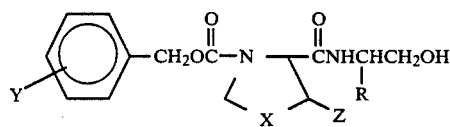

TABLE I

Ion Uptake by Corn Root Sections Treated with Test Compounds

| Compound (Example) | Substituents | | | | NO$_3^\ominus$ Reductase (percent increase over control) | Ion Uptake (percent increase over control) | | |
| --- | --- | --- | --- | --- | --- | --- | --- | --- |
| | X | Y | Z | R | | NH$_4^\oplus$ | $^{36}$ClO$_3^\ominus$ | NO$_3^\ominus$ |
| 1 | CH$_2$ | H | H | i-Bu | −1 | 80 | 26 | 40 |
| 2 | CH$_2$ | H | H | i-Pr | 7 | 100 | 56 | 65 |
| 4 | CH$_2$ | H | H | H | 4 | — | 24 | 30 |
| 5 | CH$_2$ | H | H | CH$_3$ | — | — | 20 | — |
| 6 | CH$_2$ | H | H | C$_2$H$_5$ | — | — | 20 | 24 |
| 7 | CH$_2$ | H | H | C$_2$H$_5$ | — | — | 40 | 41 |
| 8 | CH$_2$ | H | H | i-Pr | — | — | 12 | — |
| 9 | CH$_2$ | H | H | i-Pr | — | — | 37 | — |
| 10 | CH$_2$ | H | H | i-Pr | — | — | 41 | 36 |
| 11 | S | H | H | i-Pr | — | — | 35 | 31 |
| 12 | O | H | H | i-Pr | — | — | 18 | — |
| 13 | O | H | CH$_3$ | i-Pr | — | — | 20 | — |
| 15 | CH$_2$ | p-F | H | i-Pr | — | — | 35 | 30 |
| 16 | CH$_2$ | p-Cl | H | i-Pr | — | — | 14 | — |
| 17 | CH$_2$ | p-CH$_3$ | H | i-Pr | — | — | 35 | 39 |

Nitrate ion uptake enhancement activity of N-carbobenzoxy-L-prolyl-L-valinol was evaluated with other selected crops, and results are summarized in Table II. Significant stimulation of uptake was found with corn, barley and wheat, while rice, sorghum, and cotton root tissues were insensitive.

TABLE II

Nitrate Ion Uptake by Plant Root Sections Treated with 50 ppm N—carbobenzoxy-L-prolyl-L-valinol

| Crop | Ion Uptake (percent increase over control) |
| --- | --- |
| Corn | 65 |
| Barley | 75 |
| Wheat | 55 |
| Rice | 10 |
| Sorghum | −5 (decrease) |
| Cotton | −10 (decrease) |

2. Greenhouse Tests

Greenhouse tests were conducted by germinating corn seeds in a 25.4 cm pot containing a commercial potting soil mixture. After two weeks, seedlings were culled, leaving two plants in each pot. Distilled water was applied to maintain moisture levels and to leach carry-over nutrients from the potting soil mixtures. The remaining corn plants were randomized and divided into several groups for testing. Each test plant received a single 10 ml application of a test compound at 50 ppm, which was applied from a hand-held air-pressurized sprayer while the plant was rotated on a turntable in a spray hood. Each test compound was dissolved in a solution containing 50% (by volume) water and 50% AGWT diluent. AGWT diluent contains acetone, glycerol, water and polyoxyethylene sorbitan monolaurate in a volumetric ratio of 459:20:500:1.

250 mL of a complete, nitrate ion-free, potassium ion-free, and phosphate ion-free Hoagland nutrient solution were added to each pot twice weekly. This nutrient solution was supplemented with distilled water to maintain proper soil moisture. Growth and development of plants were observed in the greenhouse. Plants were allowed to grow to maturity and yields were measured at the conclusion of each test.

A spray containing 50 ppm N-carbobenzoxy-L-prolyl-L-leucinol (Example 1) stimulated growth of 2-week old corn plants deficient in nitrate ion. A similar stimulating effect was observed with N-carbobenzoxy-L-prolyl-L-valinol (Example 2).

3. Field Tests

Field tests were conducted by seeding corn (Pioneer Hybrid 3535) at a rate sufficient to obtain an excess plant population. The resulting population was thinned after emergence, 14 days after planting, to a density of about 64,000 plants per hectare, with plants about 20 cm apart in each row. The test population was subjected to severe nitrogen stress during development because only 67 kg nitrogen/hectare (60 lb/acre) were applied at planting. Nitrogen stress symptoms were apparent on lower plant leaves 32 days after emergence. Test compounds were applied to plants 34 days after emergence and 26 days prior to anthesis. Average canopy height at time of treatment was 85 cm.

The treatments were applied from an acetone/water (1:3) solution with 0.2% added nonionic surfactant, using a hand-held nitrogen-pressurized sprayer. One day following treatment, an application of about 34 kg/ha (30 lb/acre) ammonium nitrate was broadcast on the ground and immediately worked into the root zone by irrigation.

A 6.3 percent statistically significant (p=0.05) increase in grain yield of field grown corn plants was obtained (248 bushels/ha vs. 232 bushels/ha for the control) when test plants were sprayed with 500 ppm (0.14 kg/ha) N-carbobenzoxy-L-prolyl-L-valinol (Example 2).

In a second round of field tests, test plants were treated in separate experiments with N-carbobenzoxy-L-prolyl-L-valinol (Example 2) at application rates of 0.035, 0.07 and 0.14 kg/ha. Treatment at all three application rates resulted in an 8–10 percent increase in grain yield for the test plants (average 348 bushels/ha) compared with controls (average 321 bushels/ha).

What is claimed is:

1. A compound of the formula

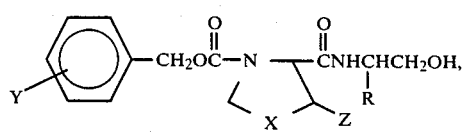

wherein

X is $CH_2$, O or S;

Y is H or an ortho, meta or para substituent selected from the group consisting of F, Cl, and alkyl groups of 1 to 4 carbons;

Z is H or $CH_3$; and

R is H or an alkyl group of 1 to 4 carbons.

2. A compound according to claim 1 wherein X is $CH_2$ and Z is H.

3. A compound according to claim 2 wherein Y is H.

4. A compound according to claim 3 wherein R is an alkyl group of 1 to 4 carbons.

5. A compound according to claim 4 wherein R is an isopropyl group.

6. A compound according to claim 4 wherein R is an isobutyl group.

7. A compound according to claim 2 wherein Y is a para substituent selected from the group consisting of F, Cl, and alkyl groups of 1 to 4 carbons.

8. A compound according to claim 7 wherein Y is a para-F substituent.

9. A composition for enhancement of nitrate and ammonium ion uptake by plants, comprising an agriculturally acceptable diluent and an effective amount of a compound of claim 1 for ion uptake enhancement.

10. A composition for enhancement of nitrate and ammonium ion uptake by plants, comprising an agriculturally acceptable diluent and an effective amount of a compound of claim 2 for ion uptake enhancement.

11. A composition for enhancement of nitrate and ammonium ion uptake by plants, comprising an agriculturally acceptable diluent and an effective amount of a compound of claim 3 for ion uptake enhancement.

12. A composition for enhancement of nitrate and ammonium ion uptake by plants, comprising an agriculturally acceptable diluent and an effective amount of a compound of claim 4 for ion uptake enhancement.

13. A composition for enhancement of nitrate and ammonium ion uptake by plants, comprising an agriculturally acceptable diluent and an effective amount of a compound of claim 5 for ion uptake enhancement.

14. A composition for enhancement of nitrate and ammonium ion uptake by plants, comprising an agriculturally acceptable diluent and an effective amount of a compound of claim 6 for ion uptake enhancement.

15. A composition for enhancement of nitrate and ammonium ion uptake by plants, comprising an agriculturally acceptable diluent and an effective amount of a compound of claim 7 for ion uptake enhancement.

16. A composition for enhancement of nitrate and ammonium ion uptake by plants, comprising an agriculturally acceptable diluent and an effective amount of a compound of claim 8 for ion uptake enhancement.

17. A method of enhancing nitrate and ammonium ion uptake by plants, comprising contacting plants with an effective amount of a composition of claim 9.

18. A method of enhancing nitrate and ammonium ion uptake by plants, comprising contacting plants with an effective amount of a composition of claim 10.

19. A method of enhancing nitrate and ammonium ion uptake by plants, comprising contacting plants with an effective amount of a composition of claim 11.

20. A method of enhancing nitrate and ammonium ion uptake by plants, comprising contacting plants with an effective amount of a composition of claim 12.

21. A method of enhancing nitrate and ammonium ion uptake by plants, comprising contacting plants with an effective amount of a composition of claim 13.

22. A method of enhancing nitrate and ammonium ion uptake by plants, comprising contacting plants with an effective amount of a composition of claim 14.

23. A method of enhancing nitrate and ammonium ion uptake by plants, comprising contacting plants with an effective amount of a composition of claim 15.

24. A method of enhancing nitrate and ammonium ion uptake by plants, comprising contacting plants with an effective amount of a composition of claim 16.

* * * * *